United States Patent [19]

Hilfman

[11] 4,175,033
[45] Nov. 20, 1979

[54] HYDROPROCESSING OF HYDROCARBONS OVER NICKEL, MOLY, PLATINUM CATALYST

[75] Inventor: Lee Hilfman, Mount Prospect, Ill.
[73] Assignee: UOP Inc., Des Plaines, Ill.
[21] Appl. No.: 970,781
[22] Filed: Dec. 18, 1978

Related U.S. Application Data

[63] Continuation-in-part of Ser. No. 810,323, Jun. 27, 1977, Pat. No. 4,148,759, which is a continuation-in-part of Ser. No. 684,055, May 6, 1976, abandoned.

[51] Int. Cl.$^2$ .............. C10G 23/06; B01J 23/56; B01J 27/04; B01J 29/12
[52] U.S. Cl. .................. 208/143; 208/216 R; 208/255; 208/264; 252/439; 252/442; 585/259; 585/841; 585/940; 585/267
[58] Field of Search ............... 208/111, 143, 216, 255

[56] References Cited
U.S. PATENT DOCUMENTS

| | | | |
|---|---|---|---|
| 3,172,835 | 3/1965 | Scott | 208/58 |
| 3,297,564 | 1/1967 | Peck et al. | 208/111 |
| 3,365,392 | 1/1968 | Mitsche et al. | 208/138 |
| 3,709,814 | 1/1973 | Jaffe | 208/59 |
| 3,953,323 | 4/1976 | Nolan et al. | 208/255 |

Primary Examiner—Delbert E. Gantz
Assistant Examiner—G. E. Schmitkons
Attorney, Agent, or Firm—James R. Hoatson, Jr.; John G. Cutts, Jr.; William H. Page, II

[57] ABSTRACT

A process for hydrotreating (hydroprocessing) hydrocarbons and mixtures of hydrocarbons utilizing a catalytic composite comprising a combination of a nickel component, a molybdenum component and a platinum component with a zeolitic carrier material wherein said platinum component is present in an amount sufficient to result in the composite containing, on an elemental basis, about 0.2 to about 0.5 percent by weight platinum, in which process there is effected a chemical consumption of hydrogen. Hydrocarbon hydroprocesses are hydrocracking, the hydrogenation of aromatic nuclei, the ring-opening of cyclic hydrocarbons, desulfurization, denitrification, hydrogenation, etc.

10 Claims, 1 Drawing Figure

Platinum Content Of A Tri-Metallic Catalyst, Weight Percent

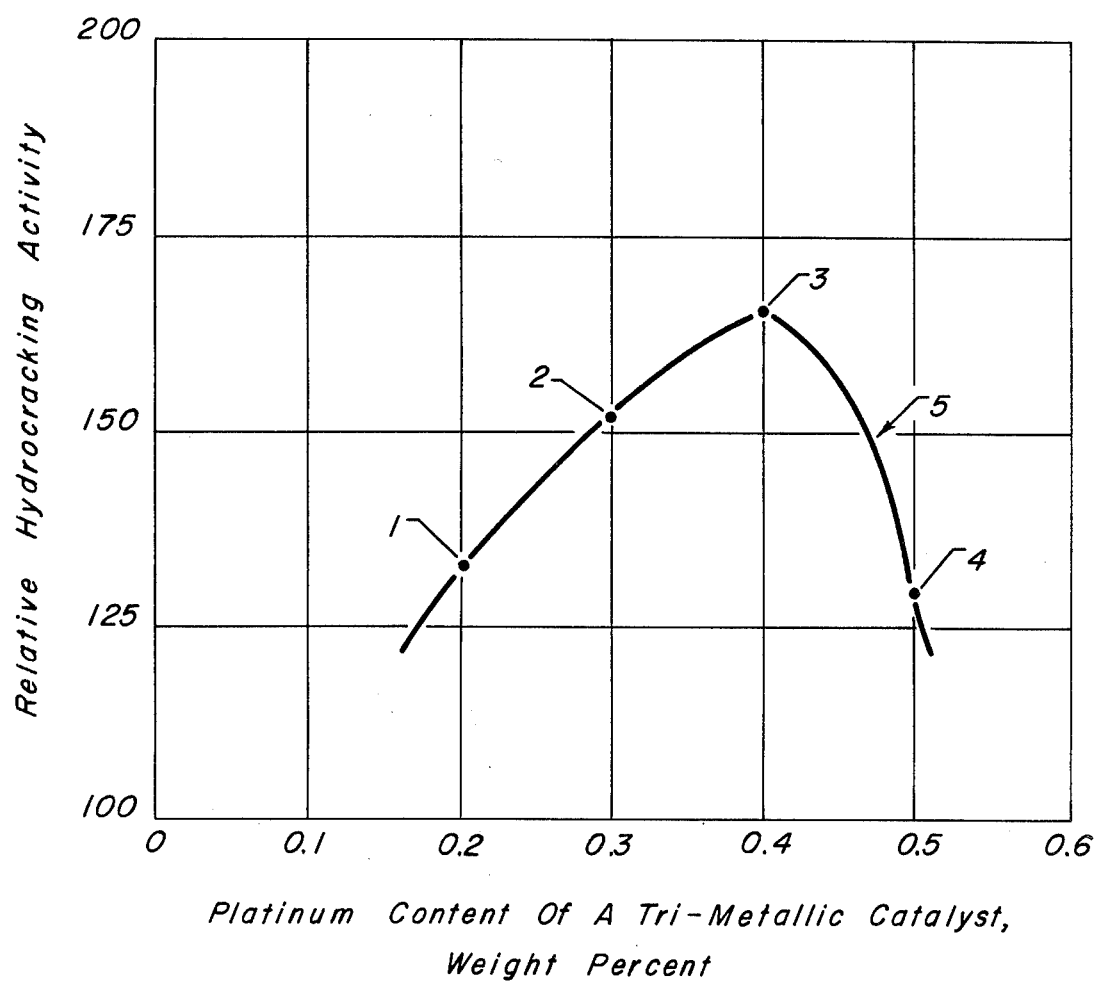

HYDROPROCESSING OF HYDROCARBONS OVER NICKEL, MOLY, PLATINUM CATALYST

CROSS-REFERENCES TO RELATED APPLICATIONS

This application is a continuation-in-part of my prior application Ser. No. 810,323 filed June 27, 1977 (U.S. Pat. No. 4,148,759) which in turn is a continuation-in-part of my prior application Ser. No. 684,055 filed May 6, 1976, and now abandoned, all the teachings of which applications are specifically incorporated by reference thereto.

APPLICABILITY OF INVENTION

The present invention encompasses the use of a catalytic composite comprising a combination of a nickel component, a molybdenum component and a platinum component with a zeolitic carrier material wherein said platinum component is present in an amount sufficient to result in the composite containing, on an elemental basis, about 0.2 to about 0.5 percent by weight platinum in the hydrotreating of hydrocarbons and mixtures of hydrocarbons. As utilized herein, the term "hydrotreating" is intended to be synonymous with the term "hydroprocessing", which involves the conversion of hydrocarbons at operating conditions selected to effect a chemical consumption of hydrogen. Included within the processes intended to be encompassed by the term "hydroprocessing" are hydrocracking, aromatic hydrogenation, ring-opening, hydrorefining (for nitrogen removal and olefin saturation), desulfurization (often included in hydrorefining) and hydrogenation, etc. As will be recognized, one common attribute of these processes, and the reactions being effected therein, is that they are all "hydrogen-consuming", and are, therefore, exothermic in nature.

The individual characteristics of the foregoing hydrotreating processes, including preferred operating conditions and techniques, will be hereinafter described in greater detail. The subject of the present invention is the use of a catalytic composite which has exceptional activity and resistance to deactivation when employed in a hydrogen-consuming process. Such processes require a catalyst having both a hydrogenation function and a cracking function. More specifically, the present process uses a dual-function catalytic composite which enables substantial improvements in those hydroprocesses that have traditionally used a dual-function catalyst. The particular catalytic composite constitutes a zeolitic carrier material, a nickel component, a molybdenum component and a platinum component; specifically, an improved hydrocracking process utilizes a crystalline aluminosilicate or zeolitic carrier material, a platinum component, a nickel component and a molybdenum component for improved activity, product selectivity and operational stability characteristics.

Composites having dual-function catalytic activity are widely employed in many industries for the purpose of accelerating a wide spectrum of hydrocarbon conversion reactions. Generally, the cracking function is thought to be associated with an acid-acting material of the porous, adsorptive refractory inorganic oxide type which is typically utilized as the carrier material for a metallic component from the metals, or compounds of metals, of Groups V through VIII of the Periodic Table, to which the hydrogenation function is generally attributed.

Catalytic composites are used to promote a wide variety of hydrocarbon conversion reactions such as hydrocracking, isomerization, dehydrogenation, hydrogenation, desulfurization, reforming, ring-opening, cyclization, aromatization, alkylation and transalkylation, polymerization, cracking, etc., some of which reactions are hydrogen-producing while others are hydrogen-consuming. In using the term "hydrogen-consuming", I intend to exclude those processes wherein the only hydrogen consumption involves the saturation of light olefins, resulting from undesirable cracking, which produces the light paraffins, methane, ethane and propane. It is to the latter group of reactions, hydrogen-consuming, that the present invention is applicable. In many instances, the commercial application of these catalysts is in processes where more than one of these reactions proceed simultaneously. An example of this type of process is a hydrocracking process wherein catalysts are utilized to effect selective hydrogenation and cracking of high molecular weight materials to produce a lower-boiling, more valuable output stream. Another such example would be the conversion of aromatic hydrocarbons into jet fuel components, principally straight, or slightly branched paraffins.

Regardless of the reaction involved, or the particular process, it is very important that the catalyst exhibit not only the capability to perform its specified functions initially, but also perform them satisfactorily for prolonged periods of time. The analytical terms employed in the art to measure how efficient a particular catalyst performs its intended functions in a particular hydrocarbon conversion process, are activity, selectivity and stability. For the purpose of discussion, these terms are conveniently defined herein, for a given charge stock, as follows: (1) activity is a measure of the ability of the catalyst to convert a hydrocarbon feed stock into products at a specified severity level, where severity level alludes to the operating conditions employed — the temperature, pressure, liquid hourly space velocity and hydrogen concentration; (2) selectivity refers to the weight percent or volume percent of the reactants that are converted into the desired product and/or products; (3) stability connotes the rate of change of the activity and selectivity parameters with time — obviously, the smaller rate implying the more stable catalyst. With respect to a hydrogen-consuming process, for example hydrocracking, activity, stability and selectivity are similarly defined. Thus, "activity" connotes the quantity of charge stock, boiling above a given temperature, which is converted to hydrocarbons boiling below the given temperature. "Selectivity" refers to the quantity of converted charge stock which boils below the desired end point of the product, as well as above a minimum specified initial boiling point. "Stability" connotes the rate of change of activity and selectivity. Thus, for example, where a gas oil, boiling above about 650° F., is subjected to hydrocracking, "activity" connotes the conversion of 650° F.-plus charge stock to 650° F.-minus product. "Selectivity" can allude to the quantity of conversion into gasoline boiling range hydrocarbons — i.e., pentanes and heavier, normally liquid hydrocarbons boiling up to about 400° F. "Stability" might be conveniently expressed in terms of temperature increase required during various increments of catalyst lift, in order to maintain the desired activity.

As is well known to those skilled in the art, the principal cause of observed deactivation or instability of a dual-function catalyst is associated with the fact that coke forms on the surface of the catalyst during the course of the reaction. More specifically, in the various hydrocarbon conversion processes, and especially those which are categorized as hydrogen-consuming, the operating conditions utilized result in the formation of high molecular weight black, solid or semi-solid, hydrogen-poor carbonaceous material which coats the surface of the catalyst and reduces its activity by shielding its active sites from the reactants. Accordingly, a major problem facing workers in this area is the development of more active and selective catalytic composites that are not as sensitive to the presence of these carbonaceous materials and/or have the capability to suppress the rate of formation of these materials at the operating conditions employed in a particular process.

I have now found a dual-function catalytic composite which possesses improved activity, selectivity and stability when employed in the hydroprocessing of hydrocarbons, wherein there is effected a chemical consumption of hydrogen. In particular, I have found that the use of a catalytic composite of a platinum component, a nickel component and a molybdenum component with a zeolitic material improves the overall operation of these hydrogen-consuming processes. Moreover, I have determined that a catalytic composite of a crystalline aluminosilicate or zeolite carrier material, a platinum component, a nickel component and a molybdenum component, when utilized in a process for hydrocracking hydrocarbonaceous material into lower-boiling hydrocarbon products, affords substantial improvement in performance and results. As indicated, the present invention essentially involves the use of a catalyst which enables the performance characteristics of the process to be sharply and materially improved.

I have discovered an improved catalyst comprising nickel-molybdenum-platinum on a zeolitic support or carrier material. More specifically, I have discovered that an unusually superior catalyst results if the platinum content is from about 0.2 to about 0.5 weight percent on an elemental basis. The criticality of the range of the platinum concentration is further illustrated hereinbelow.

A particularly preferred catalyst support or base comprises a zeolite and alumina. In addition to the foregoing compositional limitations, it is important that the catalyst base have adequate pore volume, that is, a pore volume of at least 0.5 cc/g and preferably at least 0.6 cc/g or even 0.7 cc/g.

The zeolite-alumina catalyst base is preferably in the zerogel state, that is, it is dried sufficiently to afford the usual microporous structure and therefore an appreciable available surface.

The catalyst of the present invention can be utilized to achieve the maximum production of LPG (liquefied petroleum gas) in the propane/butane range from naphtha or gasoline boiling range distillates. Heavier charge stocks, including kerosenes, light gas oils, heavy gas oils, full boiling range gas oils and "black oils" may be readily converted into lower-boiling normally liquid products including gasolines, kerosenes, middle distillates, lube oils, etc.

OBJECTS AND EMBODIMENTS

In one embodiment accordingly, the present invention provides a method of preparing catalytic composites having hydrocracking activity comprising the steps: (a) preparing a zeolite-alumina carrier material; (b) impregnating said zeolite-alumina carrier material with a nickel component, a molybdenum component and a platinum component in amounts sufficient to result in the composite containing, on an elemental basis, about 1 to about 15 weight percent nickel, about 1 to about 10 weight percent molybdenum and about 0.2 to about 0.5 weight percent platinum.

In a second embodiment, the present invention relates to a process for hydrocracking hydrocarbons which process comprises reacting said hydrocarbons with hydrogen in a reaction zone containing a catalytic composite prepared by a method comprising the steps: (a) preparing a zeolite-containing carrier material; (b) impregnating said carrier material with a nickel component, a molybdenum component and a platinum component in amounts sufficient to result in the composite containing, on an elemental basis, about 1 to about 15 weight percent nickel, about 1 to about 10 weight percent molybdenum and about 0.2 to about 0.5 weight percent platinum.

In a specific embodiment, the hydrocracking conditions include a maximum catalyst bed temperature of about 600° F. to about 900° F., a pressure of about 500 to about 5000 psig., a liquid hourly space velocity of about 0.1 to about 10 and a hydrogen circulation rate in the range of about 1000 to about 50,000 scf./bbl.

A specific object of my invention resides in the improvement of hydrogen-consuming processes including hydrocracking, hydrorefining, ring-opening for jet fuel production, hydrogenation of aromatic hydrocarbons, desulfurization, denitrification, etc. Therefore, in one embodiment, the present invention encompasses a hydrocarbon hydroprocess which comprises reacting a hydrocarbon with hydrogen at conditions selected to effect chemical consumption of hydrogen and in contact with a catalytic composite comprising a combination of a nickel component, a molybdenum component and a platinum component with a zeolitic carrier material wherein said platinum component is present in an amount sufficient to result in the composite containing, on an elemental basis, about 0.2 to about 0.5 percent by weight platinum. In another embodiment, the operating conditions include a pressure of from 400 to about 5,000 psig., an LHSV (defined as volumes of liquid hydrocarbon charge per hour per volume of catalyst disposed in the reaction zone) of from 0.1 to about 10.0, a hydrogen circulation rate of from 1,000 to about 50,000 scf./Bbl. and a maximum catalyst temperature of from 200° F. to about 900° F.

In another embodiment, the process is further characterized in that the catalytic composite is reduced and sulfided prior to contacting the hydrocarbon feed stream. In still another embodiment, my invention involves a process for hydrogenating a coke-forming hydrocarbon distillate containing di-olefinic and mono-olefinic hydrocarbons, and aromatics, which process comprises reacting said distillate with hydrogen, at a temperature below about 500° F., in contact with a catalytic composite of a zeolite-containing refractory inorganic oxide, a platinum component, an alkali metal component, a nickel component and a molybdenum component, and recovering an aromatic/mono-olefinic hydrocarbon concentrate substantially free from conjugated di-olefinic hydrocarbons.

Another embodiment affords a catalytic composite comprising a substantially pure crystalline aluminosilicate material, at least about 90.0% by weight of which is zeolitic, a platinum component, a nickel component and a molybdenum component.

Other objects and embodiments of my invention relate to additional details regarding preferred catalytic ingredients, the concentration of components in the catalytic composite, methods of catalyst preparation, individual operating conditions for use in the various hydrotreating processes, preferred processing techniques and the like particulars which are hereinafter given in the following, more detailed summary of my invention.

SUMMARY OF THE INVENTION

As hereinbefore set forth, the present invention involves the hydroprocessing of hydrocarbons and mixtures of hydrocarbons, utilizing a particular catalytic composite. This catalyst comprises a porous zeolitic carrier material having combined therewith a platinum component, a nickel component and a molybdenum component; in many applications, the catalytic composite will also contain a halogen component, and in some select applications, an alkali metal or alkaline-earth metal component.

Catalytic composites, tailored for the conversion of hydrocarbonaceous material and particularly those intended for utilization in a hydrocracking process, have traditionally consisted of metallic elements chosen from Group VIII of the Periodic Table; however, metallic components from Group VIB are quite often incorporated therein. In those instances where hydrocracking is intended to be accompanied by some hydrorefining (desulfurization, denitrification, etc.) the preferred metallic components have been nickel and molybdenum, and nickel and tungsten, which components are usually combined with a porous carrier material comprising both alumina and silica, either amorphous or zeolitic in nature. Ample evidence may be found in the literature which confirms the ability of the nickel component to effect both cracking and hydrogenation reactions.

I have found that a particularly effective zeolite-nickel-molybdenum-platinum hydrocracking catalyst can be prepared when the platinum content of the finished catalyst is maintained within the critical range of from about 0.2 to about 0.5 weight percent. Thus, it is now possible to prepare a more active and stable hydrocracking catalyst.

As is customary in the art of catalysis, when referring to the catalytically active metal, or metals, it is intended to encompass the existence of such metal in the elemental state or in some form such as an oxide, sulfide, halide, etc. Regardless of the state in which the metallic components actually exist, the concentrations are computed as if they existed in the elemental state.

The zeolite carrier material may be prepared and utilized as spheres, pills, pellets, extrudates, granules, etc. The carrier material may be prepared in any suitable manner and may be activated prior to use by one or more treatments including drying, calcination, steaming, etc. Although generally existing in some combined form, the concentration of the catalytically active metallic components is calculated on the basis of the elemental metals. Suitable hydrocracking catalysts will contan from about 0.01% to about 30% by weight of one or more metals, or compounds thereof. Another constituent of hydrocracking catalysts is a halogen component. While the precise form of association of the halogen component of the carrier material is not accurately known, it is customary in the art to refer to the halogen component as being combined with the carrier or with the other ingredients of the catalyst therein. Combined halogen may be either fluorine, chlorine, iodine, bromine or mixtures thereof; of these, fluorine and chlorine are particularly preferred. The halogen will be composited with the carrier material in such a manner as results in a final catalytic composite containing from about 0.1% to about 2% by weight of a halogen component, calculated as the element.

The metallic components may be incorporated within the catalytic composite in any suitable manner including ion-exchange or impregnation of the carrier, and either after or before calcination. The preferred method for the incorporation of the metallic components is to impregnate the carrier material with an aqueous solution of nickel and molybdenum salts and then after drying and calcining, the platinum component is added with a separate impregnation with an aqueous solution of a chloroplatinic acid. Although the metallic components may be incorporated in any manner, it is believed that the two-step impregnation method hereinabove described yields a superior hydrocracking catalyst. Even though the reasons for such a superior catalyst are uncertain, it is believed that the incorporation of the platinum metal component subsequent to the incorporation of the molybdenum component results in the construction of the most favorable metallic clusters utilized in hydrocracking reactions.

Following the incorporation of the metallic components, the carrier material is dried and subjected to a high temperature calcination or oxidation technique at a temperature of about 750° F. to about 1000° F. One particularly preferred catalyst preparation technique involves the water-free reduction of the calcined composite. This particular step is designed to insure a more uniform and finely divided dispersion of the metallic components throughout the carrier material. Substantially pure and dry hydrogen, containing less than 30 volume ppm. of water is utilized as the reducing agent. The reduced catalytic composite is then subjected to a presulfiding technique to incorporate from about 0.05% to about 3.0% by weight of sulfur, on an elemental basis, within the final catalytic composite.

The catalyst composite, prepared in accordance with the method of this invention, is preferably employed in a reaction zone as a fixed bed. The hydrocarbon charge stock after being combined with hydrogen in an amount of from about 2000 to about 20,000 standard cubic feet per barrel, and preferably at least about 5000 standard cubic feet per barrel, is introduced into the reaction zone. The charge stock may be in a liquid, or liquid-vapor phase mixture, depending upon the temperature, pressure, proportion of hydrogen and the boiling range of the charge stock being processed. The liquid hourly space velocity through the reaction zone will be in excess of about 0.2 and generally in the range of from about 1 to about 15. The source of hydrogen being admixed with a hydrocarbon charge stock may comprise a hydrogen-rich gas stream which is withdrawn from a high-pressure, low-temperature separation zone and recycled to supply at least a portion of such hydrogen. Excess hydrogen resulting from the various dehydrogenation reactions effected in a catalytic reforming unit may also be employed in admixture with the hydrocarbon charge. The reaction zone will operate under an imposed pressure within the range of from about 80 to about 3000 psig. The catalyst bed inlet temperature is maintained within the range of from about 350° to about 800° F. Since the hydrocracking reactions are exothermic, the outlet temperature or the temperature at the bottom of the catalyst bed will be significantly higher than that at the inlet thereto. The degree of exothermicity exhibited by the temperature rise across the catalyst bed is at least partially dependent upon the character of the charge stock passing therethrough, the rate at which the normally liquid hydrocarbon charge contacts the catalyst bed, the intended degree of conversion to lower-boiling hydrocarbon products, etc. In any event, the catalyst bed inlet temperature will be such that the exothermicity of the reactions taking place does not cause the temperature at the outlet of the bed to exceed about 900° F., and preferably 850° F. The operation may also be effected as a moving-bed type, or suspensoid type of operation in which the catalyst, hydrocarbon and hydrogen are admixed and passes as a slurry through the reaction zone.

Although the method of preparing the catalyst, and careful selection of operating conditions within the ranges hereinbefore set forth, extend the effective life of the catalyst composite, regeneration thereof may eventually become desired due to the natural deterioration of the catalytically active metallic components. The catalytic composite is readily regenerated by treating the same in an oxidizing atmosphere, at a temperature of from about 750° F. to about 850° F., and burning coke and other heavy hydrocarbonaceous material therefrom. The catalyst composite may then be subjected to the reducing in hydrogen, in situ, at a temperature up to about 1000° F. If desirable, the catalyst may then be sulfided in the same manner as fresh catalyst as hereinbefore described.

In embodiments of the present invention wherein the instant trimetallic catalytic composite is used for the hydrogenation of hydrogenatable hydrocarbons, it is ordinarily a preferred practice to include an alkali or alkaline earth metal component in the composite. More precisely, this optional component is selected from the group consisting of the compounds of the alkali metals— cesium, rubidium, potassium, sodium, and lithium—and the compounds of the alkaline earth metals—calcium, strontium, barium and magnesium. Generally, good results are obtained in these embodiments when this component constitutes about 1 to about 5 weight percent of the composite, calculated on an elemental basis. This optional alkali or alkaline earth metal component can be incorporated in the composite in any of the known ways, with impregnation with an aqueous solution of a suitable water-soluble, decomposable compound being preferred.

An optional ingredient for the trimetallic catalyst of the present invention is a Friedel-Crafts metal halide component. This ingredient is particularly useful in hydrocarbon conversion embodiments of the present invention wherein it is preferred that the catalyst utilized has a strong acid or cracking function associated therewith — for example, an embodiment wherein hydrocarbons are to be hydrocracked or isomerized with the catalyst of the present invention. Suitable metal halides of the Friedel-Crafts type include aluminum chloride, aluminum bromide, ferric chloride, ferric bromide, zinc chloride and the like compounds, with the aluminum halides and particularly aluminum chloride ordinarily yielding best results. Generally, this optional ingredient can be incorporated into the composite of the present invention by any of the conventional methods for adding metallic halides of this type; however, best results are ordinarily obtained when the metallic halide is sublimed onto the surface of the carrier material according to the preferred method disclosed in U.S. Pat. No. 2,999,074. The component can generally be utilized in any amount which is catalytically effective, with a value selected from the range of about 1 to about 100 weight percent of the carrier material generally being preferred. When used in many of the hydrogen-consuming processes hereinbefore described, the foregoing quantities of metallic components will be combined with a carrier material of alumina and silica, wherein the silica concentration is 10% to about 90% by weight.

According to the present invention, a hydrocarbon charge stock and hydrogen are contacted with a trimetallic catalyst of the type described in a hydrocarbon conversion zone. This contacting may be accomplished by using the catalyst in a fixed bed system, a moving bed system, a fluidized bed system, or in a batch type operation; however, in view of the danger of attrition losses of the valuable catalyst and of well known operational advantages, it is preferred to use a fixed bed system. In this system, a hydrogen-rich gas and the charge stock are preheated by any suitable heating means to the desired reaction temperature and then are passed into a conversion zone containing a fixed bed of the catalyst type previously characterized. It is, of course, understood that the conversion zone may be one or more separate reactors with suitable means therebetween to insure that the desired conversion temperature is maintained at the entrance to each reactor. It is also important to note that the reactants may be contacted with the catalyst bed in either upward, downward, or radial flow fashion with the latter being preferred. In addition, the reactants may be in the liquid phase, a mixed liquid-vapor phase, or a vapor phase when they contact the catalyst.

In some of the hydrocarbon hydroprocesses encompassed by the present invention, and especially where hydrocracking a heavy hydrocarbonaceous material to produce lower-boiling hydrocarbon products, that portion of the normally liquid product effluent boiling above the end point of the desired product will be recycled to combine with the fresh hydrocarbon charge stock. In these situations, the combined liquid feed ratio (defined as volumes of total liquid charge to the reaction zone per volume of fresh feed charge to the reaction zone) will be within the range of about 1.1 to about 6.0

The drawing included in the instant application is for the purpose of visually demonstrating the improvements and advantages afforded by the manufacture of zeolite-nickel-molybdenum-platinum hydrocracking catalyst according to the present invention.

The following examples are presented in illustration of the catalyst of this invention and is not intended as an undue limitation on the generally broad scope of the invention as set out in the appended claims.

EXAMPLE I

This example describes the preparation and testing of four zeolite-nickel-molybdenum-platinum catalysts each of which has an extruded carrier material containing 25% alumina and 75% faujasite, 5% nickel, 2% molybdenum and which contain 0.2, 0.3, 0.4 and 0.5 weight percent platinum, respectively. The extruded alumina-faujasite carrier material was initially impregnated with an aqueous solution containing soluble nickel and molybdenum salts in sufficient concentration to yield a finished catalyst with the desired nickel and molybdenum concentrations. The freshly impregnated support was then dried at about 100° C. and calcined at about 500° C. The resulting dried and calcined carrier material containing 5% nickel and 2% molybdenum was divided into five batches and four batches were impregnated with an aqueous chloroplatinic acid solution with a concentration sufficient to yield a finished catalyst with 0.2, 0.3, 0.4 and 0.5 weight percent platinum, respectively. The platinum impregnated catalysts were then dried and calcined at 100° C. and 500° C., respectively. The fifth batch was not impregnated with platinum and served as a reference catalyst for comparison purposes.

A portion of each of the five hereinabove described batches of catalyst was then used in the hydrocracking of a vacuum gas oil whose properties are summarized in Table I.

TABLE I

| PROPERTIES OF VACUUM GAS OIL | |
|---|---|
| API° Gravity at 60° F. | 33.5 |
| Distillation, °F. | |
| IBP | 290 |
| 10 | 455 |
| 30 | 596 |
| 50 | 697 |
| 70 | 762 |
| 90 | 830 |
| 95 | 870 |
| E.P. | 930 |
| % Over | 99 |
| Total Sulfur, wt. % | 0.22 |
| Total Nitrogen, ppm. | 3 |

In each case, the vacuum gas oil was processed with a reactor pressure of 1500 psig., a liquid hourly space velocity of 2.0, a hydrogen circulation rate of 10,000 scf./bbl. and at a peak catalyst bed temperature of 315° C.

The hydrocracking ability of the on-platinum containing reference catalyst was arbitrarily assigned a Relative Hydrocracking Activity of 100. Platinum containing catalysts comprising 0.2, 0.3, 0.4 and 0.5 weight percent platinum and hereinafter referred to as Catalysts 1, 2, 3, and 4, respectively, were utilized to hydrocrack the hereinbefore described vacuum gas oil and these four catalysts exhibited a Relative Hydrocracking Activity of 133, 152, 165, and 129, respectively. These data are presented in tabular form in Table II and in graphical form in the accompanying drawing.

TABLE II

| EVALUATION FOR HYDROCRACKING ACTIVITY | | | | |
|---|---|---|---|---|
| Catalyst Identity | 1 | 2 | 3 | 4 |
| Platinum Concentration, wt. % | 0.2 | 0.3 | 0.4 | 0.5 |
| Relative Hydrocracking Activity | 133 | 152 | 165 | 129 |

From the data presented in foregoing Table II and with reference to the accompanying drawing, it will be seen that the four catalysts' increasing concentrations of platinum, the latter ranging from 0.2% to 0.5% by weight, did not demonstrate linearly increasing Relative Hydrocracking Activity. This is clearly brought out upon comparing the results obtained through the use of Catalysts 1, 2, 3 and 4 which indicated a Relative Hydrocracking Activity of 133, 152, 165 and 129 respectively, for the conversion of vacuum gas oil to lower boiling hydrocarbons. Datum points 1, 2, 3 and 4 in the drawing are representative of the results obtained with Catalysts 1, 2, 3 and 4, respectively. These data were employed in preparing curve 5 of the drawing, which curve clearly illustrates the criticality attached to the platinum concentration within the range of about 0.2% to about 0.5% by weight, in order to produce a hydrocracking catalyst with superior performance characteristics. The additional economic advantages afforded through this particular result will be readily recognized by those possessing skill within the art of petroleum refining processes.

EXAMPLE II

This example describes the preparation and testing of three zeolite-nickel-molybdenum-platinum catalysts each of which has an extruded carrier material containing 25% alumina and 75% faujasite, 5% nickel, 2% molybdenum and which contain 0.2 wt. % platinum, 0.5 wt. % platinum and 0.4 wt. % palladium, respectively. The extruded alumina-faujasite carrier material was prepared in exactly the same manner as hereinabove described in Example I. The 5% nickel and 2% molybdenum was incorporated with said carrier material, also, as hereinabove described in Example I. Two portions of the resulting dried and calcined carrier material containing 5% nickel and 2% molybdenum were impregnated with an aqueous chloroplatinic acid solution with a concentration sufficient to yield a finished catalyst with 0.2 and 0.5 wt. % platinum, respectively. A third portion of the dried and calcined carrier material containing 5% nickel and 2% molybdenum was impregnated with an aqueous solution containing palladium chloride with a concentration sufficient to yield a finished catalyst with 0.4 wt. % palladium. Each of the three portions of the impregnated catalysts were then dried and calcined at 100° C. and 500° C., respectively.

The three portions of catalyst prepared as hereinabove described were then used in the hydrocracking of a vacuum gas oil whose properties are summarized in Table I. In each case, the gas oil was processed with a reactor pressure of 1500 psig., a liquid hourly space velocity of 2.0, a hydrogen circulation rate of 10,000 scf./bbl. and at a peak catalyst bed temperature of 325° C. It will be noted that catalyst bed temperature of Example I was 315° C.

The hydrocracking ability of the non-platinum and non-palladium reference catalyst of Example I was arbitrarily assigned a Relative Hydrocracking Activity of 100. Platinum containing catalysts comprising 0.2 and 0.5 wt. % platinum and palladium containing catalyst comprising 0.4 wt. % palladium hereinafter referred to as Catalysts 5, 6 and 7, respectively, were utilized to hydrocrack the hereinbefore described vacuum gas oil and these three catalysts exhibited a Relative Hydrocracking Activity of 141, 163 and 105, respectively. These data are presented in tabular form in Table III.

TABLE III

| Evaluation for Hydrocracking Activity | | | |
|---|---|---|---|
| Catalyst Identity | 5 | 6 | 7 |
| Platinum Concentration, wt. % | 0.2 | 0.5 | — |
| Palladium Concentration, wt. % | — | — | 0.4 |
| Relative Hydrocracking Activity | 141 | 163 | 105 |

The data presented in foregoing Table III illustrate that a platinum containing catalyst in the claimed critical range, viz., about 0.2 to about 0.5 wt. %, exhibits unexpected and greatly superior catalytic activity when compared with a catalyst containing palladium within the same range. When a Relative Activity comparison of 163 versus 105 can be demonstrated in the realm of catalysis, those skilled in the art will readily recognize the economic advantages afforded through the catalyst of the present invention and the fact that a randomly selected component from Group VIII or any other group will not necessarily exhibit the desired catalytic characteristics.

Specific operating conditions, processing techniques, particular catalytic composites and other individual process details will be given in the following detailed description of several of the hydrocarbon hydroprocesses to which the present invention is applicable. These will be presented by way of examples given in conjunction with commercially-scaled operating units. In presenting these examples, it is not intended that the invention be limited to the specific illustrations, nor is it intended that a given process be limited to the particular operating conditions, catalytic composite, processing techniques, charge stock, etc. It is understood, therefore, that the present invention is merely illustrated by the specifics hereinafter set forth.

EXAMPLE III

In this example, the present invention is illustrated as applied to the hydrogenation of aromatic hydrocarbons such as benzene, toluene, the various xylenes, naphthalenes, etc., to form the corresponding cyclic paraffins. When applied to the hydrogenation of aromatic hydrocarbons, which are contaminated by sulfurous compounds, primarily thiophenic compounds, the process is advantageous in that it affords 100.0% conversion without the necessity for the substantially complete prior removal of the sulfur compounds. The corresponding cyclic paraffins, resulting from the hydrogenation of the aromatic nuclei, include compounds such as cyclohexane, mono-, di-, tri-substituted cyclohexanes, decahydronapthalene, tetrahydronaphthalene, etc., which find widespread use in a variety of commercial industries in the manufacture of nylon, as solvents for various fats, oils, waxes, etc.

Aromatic concentrates are obtained by a multiplicity of techniques. For example, a benzene-containing fraction may be subjected to distillation to provide a heart-cut which contains the benzene. This is then subjected to a solvent extraction process which separates the benzene from the normal or iso-paraffinic components, and the naphthlenes contained therein. Benzene is readily recovered from the selected solvent by way of distillation, and in a purity of 99% or more. Heretofore, the hydrogenation of aromatic hydrocarbons, for example benzene, has been effected with an all nickel-containing catalyst. This is extremely disadvantageous in many respects, and especially from the standpoint that an all nickel catalyst is quite sensitive to the minor quantity of sulfurous compounds which may be contained in the benzene concentrate. In accordance with the present process, the benzene is hydrogenated in contact with a non-acidic catalytic composite containing 0.4 percent by weight platinum, 5 percent by weight nickel, 2 percent by weight molybdenum and 0.9 percent by weight of lithium, all of which are calculated on the basis of the elemental metals. Operating conditions include a maximum catalyst bed temperature in the range of about 200° F. to about 800° F., a pressure of from 500 to about 2,000 psig., a liquid hourly space velocity of about 1.0 to about 10.0 and a hydrogen circulation rate in an amount sufficient to yield a mole ratio of hydrogen to cyclohexane, in the product effluent from the last reaction zone, not substantially less than about 4.0:1. Although not essential, one preferred operating technique involves the use of three reaction zones, each of which contains approximately one-third of the total quantity of catalyst employed. The process is further facilitated when the total fresh benzene is added in three approximately equal portions, one each to the inlet of each of the three reaction zones.

The hydrogenation process will be described in connection with a commercially-scaled unit having a total fresh benzene feed capacity of about 1,488 barrels per day. Make-up gas in an amount of about 741.6 mols/hr. is admixed with 2,396 Bbl./day (about 329 mols/hr.) of a cyclohexane recycle stream, the mixture being at a temperature of about 137° F., and further mixed with 96.24 mols/hr. (582 Bbl./day) of the benzene feed; the final mixture constitutes the total charge to the first reaction zone.

Following suitable heat-exchange with various hot effluent streams, the total feed to the first reaction zone is at a temperature of 385° F. and a pressure of 460 psig. The reaction zone effluent is at a temperature of 606° F. and a pressure of about 450 psig. The total effluent from the first reaction zone is utilized as a heat exchange medium, in a steam generator, whereby the temperature is reduced to a level of about 545° C. The cooled effluent is admixed with about 98.5 moles per hour (596 Bbl./day) of fresh benzene feed, at a temperature of 100° F.; the resulting temperature is 400° F., and the mixture enters the second reaction zone at a pressure of about 440 psig. The second reaction zone effluent, at a pressure of 425 psig. and a temperature of 611° F., is admixed with 51.21 mols/hr. (310 Bbl/day) of fresh benzene feed, the resulting mixture being at a temperature of 578° F. Following its use as a heat-exchange medium, the temperature is reduced to 400° F., and the mixture enters the third reaction zone at a pressure of 415 psig. The third reaction zone effluent is at a temperature of about 509° F. and a pressure of about 400 psig. Through utilization as a heat-exchange medium, the temperature is reduced to a level of about 244° F., and subsequently reduced to a level of about 115° F. by use of an air-cooled condenser. The cooled third reaction zone effluent is introduced into a high pressure separator, at a pressure of about 370 psig.

A hydrogen-rich vaporous phase is withdrawn from the high pressure separator and recycled by way of compressive means, at a pressure of about 475 psig., to the inlet of the first reaction zone. A portion of the normally liquid phase is recycled to the first reaction zone as the cyclohexane concentrate hereinbefore described. The remainder of the normally liquid phase is passed into a stabilizing column functioning at an operating pressure of about 250 psig., a top temperature of about 160° F. and a bottom temperature of about 430° F. The cyclohexane product is withdrawn from the stabilizer as a bottoms stream, the overhead stream being vented to fuel. The cyclohexane concentrate is recovered in an amount of about 245.80 moles per hour, of which only about 0.60 moles per hour constitutes other hexanes. In brief summation, of the 19,207 pounds per hour of fresh benzene feed, 20,685 pounds per hour of cyclohexane product is recovered.

EXAMPLE IV

Another hydrocarbon hydroprocessing scheme, to which the present invention is applicable, involves the hydrorefining of coke-forming hydrocarbon distillates. These hydrocarbon distillates are generally sulfurous in nature, and contain mono-olefinic, di-olefinic and aromatic hydrocarbons. Through the utilization of a catalytic composite comprising a nickel component, a molybdenum component and a platinum component, increased selectivity and stability of operation is obtained; selectivity is most noticeable with respect to the retention of aromatics, and in hydrogenating conjugated di-olefinic and mono-olefinic hydrocarbons. Such charge stocks generally result from diverse conversion processes including the catalytic and/or thermal cracking of petroleum, sometimes referred to as pyrolysis, the destructive distillation of wood or coal, shale oil retorting, etc. The impurities in these distillate fractions must necessarily be removed before the distillates are suitable for their intended use, or which when removed, enhance the value of the distillate fraction for further processing. Frequently, it is intended that these charge stocks be substantially desulfurized, saturated to the extent necessary to remove the conjugated di-olefins, while simultaneously retaining the aromatic hydrocarbons. When subjected to hydrorefining for the purpose of removing the contaminating influences, there is encountered difficulty in effecting the desired degree of reaction due to the formation of coke and other carbonaceous material.

As utilized herein, "hydrogenating" is intended to be synonymous with "hydrorefining". The purpose is to provide a highly selective and stable process for hydrogenating coke-forming hydrocarbon distillates, and this is accomplished through the use of a fixed-bed catalytic reaction system utilizing a catalyst comprising a nickel component, a molybdenum component and a platinum component. There exists two separate, desirable routes for the treatment of coke-forming distillates, for example a pyrolysis naphtha by-product. One such route is directed toward a product suitable for use in certain gasoline blending. With this as the desired object, the process can be effected in a single stage, or reaction zone, with the catalytic composite hereinafter specifically described as the first-stage catalyst. The attainable selectivity in this instance resides primarily in the hydrogenation of highly reactive double bonds. In the case of conjugated di-olefins, the selectivity afforded restricts the hydrogenation to produce mono-olefins, and, with respect to the styrenes, for example, the hydrogenation is inhibited to produce alkyl benzenes without "ring" saturation. The selectivity is accomplished with a minimum of polymer formation either to "gums", or lower molecular weight polymers which would necessitate a re-running of the product before blending to gasoline would be feasible. Other advantages of restricting the hydrogenating of the conjugated di-olefins, such as.1,5 normal hexadiene are not unusually offensive in suitably inhibited gasolines in some locales, and will not react in this first stage. Some fresh charge stocks are sufficiently low in mercaptan sulfur content that direct gasoline blending may be considered, although a mild treatment for mercaptan sulfur removal might be necessary. These considerations are generally applicable to foreign markets, particularly European, where olefinic and sulfur-containing gasolines are not too objectionable. It must be noted that the sulfurous compounds, and the mono-olefins, whether virgin, or products of di-olefin partial saturation, are unchanged in the single, or first-stage reaction zone. Where however the desired end result is aromatic hydrocarbon retention, intended for subsequent extraction, the two-stage route is required. The mono-olefins must be substantially saturated in the second stage to facilitate aromatic extraction by way of currently utilized methods. Thus, the desired necessary hydrogenation involves saturation of the mono-olefins, as well as sulfur removal, the latter required for an acceptable ultimate aromatic product. Attendant upon this is the necessity to avoid even partial saturation of aromatic nuclei.

With respect to one catalytic composite, its principal function involves the selective hydrogenation of conjugated di-olefinic hydrocarbons to mono-olefinic hydrocarbons. This particular catalytic composite possesses unusual stability notwithstanding the presence of relatively large quantities of sulfurous compounds in the fresh charge stock. The catalytic composite comprises a zeolite refractory inorganic oxide, a nickel component, a molybdenum component, a platinum component and an alkali-metal component, the latter being preferably potassium and/or lithium. It is especially preferred, for use in this particular hydrocarbon hydroprocessing scheme, that the catalytic composite be substantially free from any "acid-acting" propensities. The catalytic composite, utilized in the second reaction zone for the primary purpose of effecting the destructive conversion of sulfurous compounds into hydrogen sulfide and hydrocarbons, is a composite of an alumina-zeolite refractory inorganic oxide, a platinum component, a nickel component, and a molybdenum component. Through the utilization of a particular sequence of processing steps, and the use of the foregoing described catalytic composites, the formation of high molecular weight polymers and co-polymers is inhibited to a degree which permits processing for an extended period of time. Briefly, this is accomplished by initiating the hydrorefining reactions at temperatures below about 500° F., at which temperatures the coke-forming reactions are not promoted. The operating conditions within the second reaction zone are such that the sulfurous compounds are removed without incurring the detrimental polymerization reactions otherwise resulting were it not for the saturation of the conjugated di-olefinic hydrocarbons within the first reaction zone.

The hydrocarbon distillate charge stock, for example a light naphtha by-product from a commercial cracking unit designed and operated for the production of ethylene, having a gravity of about 34.0° API, a bromine number of about 35.0, a diene value of about 17.5 and containing about 1,600 ppm. by weight of sulfur and 75.9 vol. % aromatic hydrocarbons, is admixed with recycled hydrogen. This light naphtha co-product has an initial boiling point of about 164° F. and an end boiling point of about 333° F. The hydrogen circulation rate is within the range of from about 1,000 to about 10,000 scf./Bbl., and preferably in the narrower range of from 1,500 to about 6,000 scf./Bbl. The charge stock is heated to a temperature such that the maximum catalyst temperature is in the range of from about 200° F. to about 500° F., by way of heat-exchange with various product effluent streams, and is introduced into the first reaction zone at an LHSV in the range of about 0.5 to about 10.0. The reaction zone is maintained at a pressure of from 400 to about 1,000 psig., and preferably at a level in the range of from 500 psig, to about 900 psig.

The temperature of the product effluent from the first reaction zone is increased to a level above about 500° F., and preferably to result in a maximum catalyst temperature in the range of 600° F. to 900° F. When the process is functioning efficiently, the diene value of the liquid charge entering the second catalytic reaction zone is less than about 1.0 and often less than about 0.3. The conversion of nitrogenous and sulfurous compounds, and the saturation of mono-olefins, contained within the first zone effluent, is effected in the second zone. The second catalytic reaction zone is maintained under an imposed pressure of from about 400 to about 1,000 psig., and preferably at a level of from about 500 to about 900 psig. The two-stage process is facilitated when the focal point for pressure control is the high pressure separator serving to separate the product effluent from the second catalytic reaction zone. It will, therefore, be maintained at a pressure slightly less than the first catalytic reaction zone, as a result of fluid flow through the system. The LHSV through the second reaction zone is about 0.5 to about 10.0, based upon fresh feed only. The hydrogen circulation rate will be in a range of from 1,000 to about 10,000 scf./Bbl., and preferably from about 1,000 to about 8,000 scf./Bbl. Series-flow through the entire system is facilitated when the recycle hydrogen is admixed with the fresh hydrocarbon charge stock. Make-up hydrogen, to supplant that consumed in the overall process, may be introduced from any suitable external source, but is preferably introduced into the system by way of the effluent line from the first catalytic reaction zone to the second catalytic reaction zone.

With respect to the naphtha boiling range portion of the product effluent, the sulfur concentration is about 0.1 ppm., the aromatic concentration is about 75.1% by volume, the bromine number is less than about 0.3 and the diene value is essentially "nil".

With charge stocks having exceedingly high diene values, a recycle diluent is employed in order to prevent an excessive temperature rise in the reaction system. Where so utilized, the source of the diluent is preferably a portion of the normally liquid product effluent from the second catalytic reaction zone. The precise quantity of recycle material varies from feed stock to feed stock; however, the rate at any given time is controlled by monitoring the diene value of the combined liquid feed to the first reaction zone. As the diene value exceeds a level of about 25.0, the quantity of recycle is increased, thereby increasing the combined liquid feed ratio; when the diene value approaches a level of about 20.0, or less, the quantity of recycle diluent may be lessened, thereby decreasing the combined liquid feed ratio.

With another so-called pyrolysis gasoline, having a gravity of about 34.6° API, containing 600 ppm. by weight of sulfur, 78.5% by volume of aromatics, and having a bromine number of 45 and a diene value of 25.5 it is initially processed in a first reaction zone containing a catalytic composite of alumina-zeolite, 0.5% by weight of lithium, 0.20% by weight of platinum, 5% by weight of nickel and 2% by weight of molybdenum, calculated as the elements. The fresh feed charge rate is 3,300 Bbl./day, and this is admixed with 2,475 Bbl./day of the normally liquid diluent. Based upon fresh feed only, the LHSV is 2.5 and the hydrogen circulation rate is 1,750 scf./Bbl. The charge is raised to a temperature of about 250° F., and enters the first reaction zone at a pressure of about 840 psig. The product effluent emanates from the first reaction zone at a pressure of about 830 psig. and a temperature of about 350° F. The effluent is admixed with about 660 scf./Bbl. of make-up hydrogen, and the temperature is increased to a level of about 545° F., the heated stream is introduced into the second reaction zone under a pressure of about 790 psi. The LHSV, exclusive of the recycle diluent, is 2.5, and the hydrogen circulation rate is about 1,500. The second reaction zone contains a catalyst of a composite of alumina-zeolite, 0.375% by weight of platinum, 5% by weight of nickel and 2% by weight of molybdenum. The reaction product effluent is introduced, following its use as a heat-exchange medium and further cooling to reduce its temperature from 620° F. to a level of 100° F., into a high-pressure separator at a pressure of about 750 psig. The normally liquid stream from the cold separator is introduced into a reboiled stripping column for hydrogen sulfide removal and depentanization. The hydrogen sulfide stripping column functions at conditions of temperature and pressure required to concentrate a $C_6$ to $C_9$ aromatic stream as a bottoms fraction. With respect to the overall product distribution, only 690 lbs./hr. of pentanes and lighter hydrocarbons is indicated in the stripper overhead. The aromatic concentrate is recovered in an amount of about 40,070 lbs./hr. (the fresh feed is 40,120 lbs./hr.); these results are achieved with a hydrogen consumption of only 660 scf./Bbl. With respect to the desired product, the aromatic concentration is 78.0, the sulfur concentration is less than 1.0 ppm. by weight, and the diene value is essentially "nil".

EXAMPLE V

This example is presented to illustrate still another hydrocarbon hydroprocessing scheme for the improvement of the jet fuel characteristics of sulfurous kerosene boiling range fractions. The improvement is especially noticeable in the IPT Smoke Point, the concentration of aromatic hydrocarbons and the concentration of sulfur. A two-stage process wherein desulfurization is effected in the first reaction zone at relatively mild severities which result in a normally liquid product effluent containing from about 15 to about 35 ppm. of sulfur by weight. Aromatic saturation is the principal reaction effected in the second reaction zone, having disposed therein a catalytic composite of alumina-zeolite, a halogen component, a platinum component, a nickel component and a molybdenum component.

Suitable charge stocks are kerosene fractions having an initial boiling point as low as about 300° F., and an end boiling point as high as about 575° F., and, in some instances, up to 600° F. Examplary of such kerosene fractions are those boiling from about 300° F. to about 550° F., from 330° F. to about 500° F., from 330° F. to about 530° F., etc. As a specific example, a kerosene obtained from hydrocracking a Mid-continent slurry oil, having a gravity of about 30.5° API, an initial boiling point of about 388° F., an end boiling point of about 522° F., has an TPT Smoke Point of 17.1 mm., and contains 530 ppm. of sulfur and 24.8% by volume of aromatic hydrocarbons. Through the use of the catalytic process of the present invention, the improvement in the jet fuel quality of such a kerosene fraction is most significant with respect to raising the IPT Smoke Point, and reducing the concentration of sulfur and the quantity of aromatic hydrocarbons. Specifications regarding the poorest quality of jet fuel, commonly referred to as Jet-A, Jet-Al and Jet-B call for a sulfur concentration of about 0.3% by weight maximum (3,000 ppm.), a minimum IPT Smoke Point of 25 mm. and a maximum aromatic concentration of about 20.0 vol. %.

The charge stock is admixed with circulating hydrogen in an amount within the range of from about 1,000 to about 2,000 scf./Bbl. This mixture is heated to a temperature level necessary to control the maximum catalyst bed temperature below about 750° F., and preferably not above 700° F., with a lower catalyst bed temperature of about 600° F. The catalyst, a well known standard desulfurization catalyst containing about 2.2% by weight of cobalt and about 5.7% by weight of molybdenum, composited with alumina is disposed in a reaction zone maintained under an imposed pressure in the range of from about 500 to about 1,100 psig. The LHSV is in the range of about 0.5 to about 10.0, and preferably from about 0.5 to about 5.0. The total product effluent from this first catalytic reaction zone is separated to provide a hydrogen-rich gaseous phase and a normally liquid hydrocarbon stream containing 15 ppm. to about 35 ppm. of sulfur by weight. The normally liquid phase portion of the first reaction zone effluent is utilized as the fresh feed charge stock to the second reaction zone. In this particular instance, the first reaction zone decreases the sulfur concentration to about 25 ppm., the aromatic concentration to about 16.3% by volume, and has increased the IPT Smoke Point to a level of about 21.5 mm.

The catalytic composite within the second reaction zone comprises alumina-zeolite, 0.375% by weight of platinum, 5% by weight of nickel, 2% by weight of molybdenum and about 0.60% by weight of combined chloride, calculated on the basis of the elements. The reaction zone is maintained at a pressure of about 400 to about 1,500 psig., and the hydrogen circulation rate is in the range of 1,500 to about 10,000 scf./Bbl. The LHSV, hereinbefore defined, is in the range of from about 0.5 to about 5.0, and preferably from about 0.5 to about 3.0. It is preferred to limit the catalyst bed temperature in the second reaction zone to a maximum level of about 750° F. With a catalyst of this particular chemical and physical characteristics, optimum aromatic saturation, processing a feed stock containing from about 15 to about 35 ppm. of sulfur, is effected at maximum catalyst bed temperatures in the range of about 625° F. to about 750° F. With respect to the normally liquid kerosene fraction, recovered from the condensed liquid removed from the total product effluent, the sulfur concentration is effectively "nil", being about 0.1 ppm. The quantity of aromatic hydrocarbons has been decreased to a level of about 0.75% by volume, and the IPT Smoke Point has been increased to about 36.3 mm.

With respect to another kerosene fraction, having an IPT Smoke Point of about 20.5 mm., an aromatic concentration of about 19.3 vol.% and a sulfur concentration of about 17 ppm. by weight, the same is processed in a catalytic reaction zone at a pressure of about 850 psig. and a maximum catalyst bed temperature of about 725° F. The LHSV is about 1.35, and the hydrogen circulation rate is about 8,000 scf./Bbl. The catalytic composite disposed within the reaction zone comprises alumina-zeolite, 0.25% by weight of platinum, 5% by weight of nickel, 0.40% by weight of molybdenum, about 0.35% by weight of combined chloride and 0.35% by weight of combined fluoride. Following separation and distillation, to concentrate the kerosene fraction, analyses indicate that the Smoke Point has been increased to a level of about 36.9 mm., the aromatic concentration has been lowered to about 0.6% by volume and the sulfur concentration is essentially "nil".

EXAMPLE VI

This illustration of a hydrocarbon hydroprocessing scheme, encompassed by my invention, is one which involves hydrocracking heavy hydrocarbonaceous material into lower-boiling hydrocarbon products. In this instance, the preferred catalysts contain a nickel component, a platinum component, a molybdenum component, combined with a zeolite material, preferably faujasite, and still more preferably one which is at least 90.0% by weight zeolitic.

Most of the virgin stocks, intended for hydrocracking, are contaminated by sulfurous compounds and nitrogenous compounds, and in in the case of the heavier charge stocks, various metallic contaminants, insoluble asphalts, etc. Contaminated charge stocks are generally hydrorefined in order to prepare a charge suitable for hydrocracking. Thus, the catalytic process of the present invention can be beneficially utilized as the second stage of a two-stage process, in the first stage of which the fresh feed is hydrorefined.

Hydrocracking reactions are generally effected at elevated pressures in the range of about 800 to about 5,000 psig., and preferably at some intermediate level of 1,000 to about 3,500 psig. Liquid hourly space velocities of about 0.25 to about 10.0 will be suitable, the lower range generally reserved for the heavier stocks. The hydrogen circulation rate will be at least about 3,000 scf./Bbl., with an upper limit of about 50,000 scf./Bbl., based upon fresh feed. For the majority of feed stocks, hydrogen circulation in the range of 5,000 to 20,000 scf./Bbl. will suffice. With respect to the LHSV, it is based upon fresh feed, notwithstanding the use of recycle liquid providing a combined liquid feed ratio in the range of about 1.25 to about 6.0. The operating temperature again alludes to the temperature of the catalyst within the reaction zone, and is in the range of about 400° F. to about 900° F. Since the principal reactions are exothermic in nature, the increasing temperature gradient, experienced as the charge stock traverses the catalyst bed, results in an outlet temperature higher than that at the inlet to the catalyst bed. The maximum catalyst temperature should not exceed 900° F., and it is generally a preferred technique to limit the temperature increase to 100° F. or less.

A preferred carrier material constitutes a crystalline alumino-silicate, preferably faujasite, of which at least about 90% by weight is zeolitic. This carrier material, and a method of preparing the same, have hereinbefore been described. Generally, the nickel component will be used in an amount sufficient to result in a final catalytic composite containing about 0.01% to about 10% by weight. The molybdenum component will be used in an amount sufficient to result in a final catalytic composite containing about 0.01% to about 10% by weight. The platinum component is generally present in an amount within the range of about 0.2% to about 0.5% by weight, and may exist within the composite as a compound such as an oxide, sulfide, halide, etc. Another possible constituent of the catalyst is a halogen component, either fluorine, chlorine, iodine, bromine, or mixtures thereof. Of these, it is preferred to utilize a catalyst containing fluorine and/or chlorine. The halogen component will be composited with the carrier material in such a manner as results in a final composite containing about 0.1% to about 1.5% by weight of halogen, calculated on an elemental basis.

A specific illustration of this hydrocarbon hydroprocessing technique involves the use of a catalytic composite of about 0.4% by weight of platinum, 5% by weight of nickel, 0.7% by weight of combined chlorine, and 2% by weight of molybdenum, combined with a crystalline aluminosilicate material of which about 90.9% by weight constitutes faujasite. This catalyst is intended for utilization in the conversion of 16,000 Bbl./day of a blend of light gas oils to produce maximum quantities of a heptane-400° F. gasoline boiling range fraction. The charge stock has a gravity of 33.8° API, contains 0.19% by weight of sulfur (1,900 ppm.) and 67 ppm. by weight of nitrogen, and has an initial boiling point of 369° F., a 50% volumetric distillation temperature of 494° F. and an end boiling point of 655° F. The charge stock is initially subjected to a clean-up operation at maximum catalyst temperature of 750° F., a combined feed ratio of 1.0 an LHSV of 2.41 with a hydrogen circulation rate of about 5,000 scf./Bbl. The pressure imposed upon the catalyst within the reaction zone is about 1,500 psig. Since at least a portion of the blended gas oil charge stock will be converted into lower-boiling hydrocarbon products, the effluent from this clean-up reaction zone is separated to provide a normally liquid, 400° F.-plus charge for the hydrocracking reaction zone containing the platinum-nickel-molybdenum-chloride catalyst. The pressure imposed upon the second reaction zone is about 1,500 psig., and the hydrogen circulation rate is about 8,000 scf./Bbl. The original quantity of fresh feed to the clean-up reaction zone is about 16,000 Bbl./day; following separation of the first zone effluent to provide the 400° F.-plus charge to the second reaction zone, the charge to the second reaction zone is in an amount of about 12,150 Bbl./day, providing an LHSV of 0.85. The temperature at the inlet to the catalyst bed is 665° F., and a conventional hydrogen quench stream is utilized to maintain the maximum reactor outlet temperature at about 700° F. Following separation of the product effluent from the second reaction zone, to concentrate the desired gasoline boiling range fraction, the remaining 400° F.-plus normally liquid material, in an amount of 7,290 Bbl./day, is recycled to the inlet of the second reaction zone, thus providing a combined liquid feed ratio thereto of about 1.60. In the following table, there is indicated the product yield and distribution of this process. With respect to normally liquid hydrocarbons, for convenience including butanes, the yields are given in vol.%; with respect to the normally liquid hydrocarbons, ammonia and hydrogen sulfide, the yields are given in terms of weight percent. With respect to the first reaction zone, the hydrogen consumption is 1.31% by weight of the fresh feed (741 scf./Bbl.), and for the hydrocracking reaction, 1.26% by weight of the fresh feed charge stock, or 713 scf./Bbl.

TABLE

| Hydrocracking Product Yield and Distribution | | | |
|---|---|---|---|
| Component | Stage I | Stage II | Total |
| Ammonia | 0.01 | — | 0.01 |
| Hydrogen Sulfide | 0.21 | — | 0.21 |
| Methane | 0.12 | 0.02 | 0.14 |
| Ethane | 0.22 | 0.40 | 0.62 |
| Propane | 1.03 | 3.48 | 4.51 |
| Butanes | 3.90 | 14.66 | 18.56 |
| Pentanes | 3.04 | 11.28 | 14.32 |
| Hexanes | 3.00 | 11.21 | 14.21 |
| C$_7$-400° F. | 18.85 | 49.46 | 68.41 |
| 400° F.-plus | 75.92* | — | — |

*Charge to Stage II

With respect to both the butane product and pentane product, the former is indicated as being about 68.0% isobutanes, while the latter constitutes about 93.0% isopentanes. An analysis of the combined pentane/hexane fraction indicates a gravity of 82.6° API, a clear research octane rating of 85.0 and a leaded research octane rating of 99.0; it will be noted that this constitutes an excellent blending component for motor fuel. The desired heptane-400° F. product indicates a gravity of 48.8° API, a clear research octane rating of 72.0 and a leaded research octane rating of 88.0. This gasoline boiling range fraction constitutes about 34.0% by volume paraffins, 36.0% by volume naphthenes and 30.0% by volume aromatic hydrocarbons. It will be recognized that this gasoline boiling range fraction constitutes an excellent charge stock for a catalytic reforming unit to improve the motor fuel characteristics thereof.

The foregoing specification, and particularly the examples, indicates the method by which the present invention is effected, and the benefits afforded through the utilization thereof.

I claim as my invention:

1. A hydrocarbon hydroprocess which comprises reacting a hydrocarbon with hydrogen at conditions selected to effect chemical consumption of hydrogen, and in contact with a catalytic composite comprising a combination of a nickel component, a molybdenum component and a platinum component with a zeolitic carrier material wherein said platinum component is present in an amount sufficient to result in the composite containing, on an elemental basis, about 0.2 to about 0.5 percent by weight platinum.

2. The process of claim 1 further characterized in that said conditions include a pressure of from 400 to about 5000 psig., a liquid hourly space velocity of from about 0.1 to about 10, a hydrogen circulation rate of from 1,000 to about 50,000 scf./bbl. and a maximum catalyst temperature of from about 200° F. to about 900° F.

3. The process of claim 1 further characterized in that said catalytic composite contains from about 1% to about 15% by weight of said nickel component and from about 1% to about 10% by weight of said molybdenum component, on an elemental basis.

4. The process of claim 1 further characterized in that said catalytic composite contains from about 0.1% to about 1.5% by weight of a halogen component, on an elemental basis.

5. A hydrocarbon hydroprocess which comprises reacting a hydrocarbon with hydrogen at conditions selected to effect chemical consumption of hydrogen, and in contact with a catalytic composite of a platinum component, a nickel component, a molybdenum component and a zeolitic carrier material; said process further characterized in that said catalytic composite is reduced and sulfided prior to contacting said hydrocarbon.

6. The process of claim 5 further characterized in that said zeolitic carrier material is a faujasite.

7. The process of claim 5 further characterized in that said zeolitic carrier material is admixed with an amorphous refractory inorganic oxide.

8. A process for desulfurizing a sulfurous hydrocarbon distillate containing mono-olefinic hydrocarbons and aromatics, which process comprises reacting said distillate with hydrogen, in contact with a catalytic composite comprising a combination of a nickel component, a molybdenum component and a platinum component with a zeolitic carrier material wherein said platinum component is present in an amount sufficient to result in the composite containing, on an elemental basis, about 0.2 to about 0.5 percent by weight platinum.

9. A process for hydrogenating a coke-forming hydrocarbon distillate containing di-olefinic and mono-olefinic hydrocarbons, and aromatics, which process comprises reacting said distillate with hydrogen, at a temperature below about 500° F., in contact with a catalytic composite comprising a combination of a nickel component, a molybdenum component, a platinum component and an alkali metal component with a zeolitic carrier material wherein said platinum component is present in an amount sufficient to result in the composite containing on an elemental basis, about 0.2 to about 0.5 percent by weight platinum, and recovering an aromatic/mono-olefinic hydrocarbon concentrate substantially free from conjugated di-olefinic hydrocarbons.

10. A process for improving the jet fuel characteristics of a sulfurous kerosene boiling range fraction, which process comprises reacting said kerosene fraction and hydrogen, at a maximum catalyst temperature below about 750° F., in a catalytic reaction zone containing a catalytic composite comprising a combination of a nickel component, a molybdenum component and a platinum component with a zeolitic carrier material wherein said platinum component is present in an amount sufficient to result in the composite containing, on an elemental basis, about 0.2 to about 0.5 percent by weight platinum, and separating the resulting reaction zone effluent to recover a normally liquid kerosene fraction having improved jet fuel characteristics.

* * * * *